United States Patent [19]

Morris

[11] 4,131,739

[45] Dec. 26, 1978

[54] CATALYTIC REARRANGEMENT OF CYCLIC ACETALS TO CARBOXYLIC ESTERS

[75] Inventor: Don L. Morris, Longview, Tex.

[73] Assignee: Eastman Kodak Company, Rochester, N.Y.

[21] Appl. No.: 814,562

[22] Filed: Jul. 11, 1977

[51] Int. Cl.² ............................................. C07C 69/66
[52] U.S. Cl. .............................. 560/179; 260/345.1; 260/410.9 R; 560/103; 560/129; 560/231; 560/240; 568/907; 568/687; 568/691
[58] Field of Search ............... 560/179, 129, 103, 231, 560/240; 260/410.9 R

[56] References Cited

U.S. PATENT DOCUMENTS 3,444,238   5/1969   Weiss et al. ........................ 560/240

OTHER PUBLICATIONS

Fewlass, Chem. Absts., vol. 77, 126012p (1972).
Gove, Webster's Third New International Dictionary, G. & C Merriam, p. 120 (1963).

Primary Examiner—James O. Thomas, Jr.
Assistant Examiner—G. T. Breitenstein
Attorney, Agent, or Firm—Edward R. Weber; Daniel B. Reece, III

[57] ABSTRACT

Cyclic acetals are rearranged to form isomeric carboxylic acid esters according to the following formula:

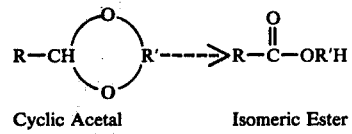

Cyclic Acetal          Isomeric Ester wherein
R is an alkyl, alkenyl, or aromatic moiety containing 1 to 12 carbon atoms;
and
R' is an alkyl or alkenyl moiety containing 1 to 12 carbon atoms;
in the presence of a catalyst consisting of a metal selected from the group Ru, Rh, Pd, Os, Ir or Pt supported on carbon.

9 Claims, No Drawings

CATALYTIC REARRANGEMENT OF CYCLIC ACETALS TO CARBOXYLIC ESTERS

This invention is concerned with a process for rearranging cyclic acetals to carboxylic acid esters. More specifically this invention is concerned with a process for rearranging cyclic acetals to carboxylic acid esters without going through an intermediate acid step and without the use of oxidizing gases or typical oxidizing reagents.

A photochemical conversion of cyclic acetals to carboxylic acid esters has been reported [D. Elad, R. Youssefyeh, Tetrahedron Letter, 30, 2189 (1963)]. The reaction was characterized by long reaction times and low yields.

Ditertiary-butyl peroxide induced conversions of cyclic acetals of benzaldehyde to benzoate esters have also been reported [E. S. Huyser and Z. Garcia, J. Org. Chem., 27, 2716 (1962)]. The reaction was carried out using 5/1, 10/1 and 21.5/1 mole ratios of acetal to peroxide. The conversion of acetal to esters was dependent on the amount of peroxide present. The reaction required long reaction times (18 hours or more) and yields of carboxylic acid esters were less than 50 percent.

The thermal rearrangement of unsaturated acetals with allyloxy structures has been reported to form allyl esters [F. Weiss and A. Issard, French Pat. No. 1,384,693, January 8, 1965; F. Mutterer, J. M. Morgan, J. M. Biederman, J. P. Fleury and F. Weiss, Tetrahedron, 26, 477 (1970); and T. L. Ho and C. M. Wong, Synthetic Communications, 5, 213 (1975)].

The rearrangement was carried out at 250° to 600° C. and was postulated to proceed through the "ene" mechanism shown below. The presence of the allyloxy acetal structure was necessary for the formation of esters.

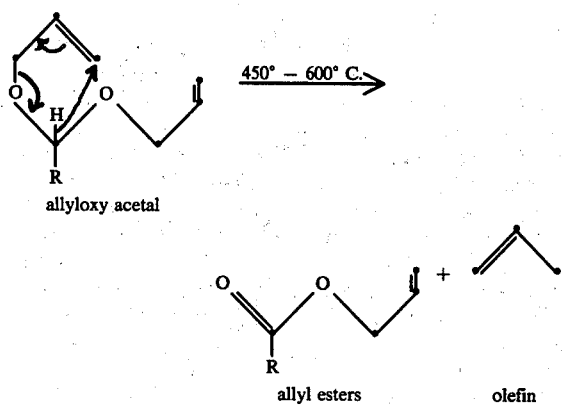

Cyclic or acyclic acetals not possessing the allyloxy structure did not result in formation of carboxylic acid esters when heated from 450° to 600° (J. P. Fluery et. al.).

It is therefore an object of this invention to produce carboxylic acid esters without the use of oxidizing gases or typical oxidizing reagents. It is a further object of this invention to provide a process for producing carboxylic acid esters without going through an intermediate carboxylic acid step. Yet another object of this invention is to provide a process for producing carboxylic acid esters in good yields. These and other objects of the invention will become apparent from the following specification and claims.

It has been discovered that cyclic acetals can be rearranged to isomeric carboxylic acid esters according to the following formula

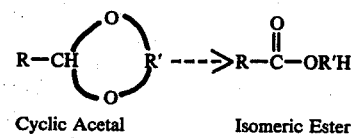

wherein

R is an alkyl, alkenyl, or aromatic moiety containing 1 to 12 carbon atoms, preferably 1 to 6 carbon atoms; and R' is an alkyl or alkenyl moiety containing 1 to 12 carbon atoms, preferably 1 to 6 carbon atoms.

The rearrangement occurs in the presence of a catalyst consisting of a metal selected from the group consisting of Ru, Rh, Pd, Os, Ir or Pt supported on carbon.

The rearrangement can be carried out in the vapor phase or in the liquid phase. When the reaction is carried out in the vapor phase the acetal vapors are allowed to pass over a bed of the catalysts at a temperature of from about 200° C. to about 400° C, preferably about 250° C. to about 350° C., and the product is collected by condensation of the vapors. This vapor phase rearrangement gives good results based on yield, selectivity and production rate.

When carried out in the vapor phase the reaction may be conducted at subatmospheric, atmospheric, or superatmospheric pressure.

The reaction may also be conducted in a liquid phase by slurrying the catalyst in the liquid acetal or by passing the liquid acetal over a fixed bed of catalyst. The acetal may be diluted with an inert solvent such as hexane, benzene or acetone or other solvent which is inert to the reactants and products under the conditions of the reaction. This is particularly beneficial when the acetal being rearranged is a solid. The temperature employed for rearrangement in the liquid phase can be from about 100° C. to about 400° C. at a pressure which maintains the acetal in the liquid phase. A preferred temperature range for the liquid phase rearrangement is from about 200° C. to about 350° C.

The product from either the vapor phase or the liquid phase rearrangement can be isolated by conventional methods including distillation, extraction or crystallization. The carboxylic acid esters recovered are generally easily separated from the unreacted acetals by distillation. The reaction is characterized by high yields and space time yields. Table I, following, demonstrates yield and conversion data for six representative cyclic acetals to carboxylic acids rearrangements.

The catalytic rearrangement reaction of the instant invention is surprising and unexpected. There is no indication in the literature that this rearrangement would occur over a platinum group catalyst. Platinum catalysts are known to catalyze a number of rearrangements, however, there is no indication that the rearrangement of the cyclic acetal to a carboxylic acid ester would occur. It is further unobvious that carbon would be a selective and specific support for the metal portion of the catalyst system. It would be assumed that other inert supports would be equally effective in a catalyst system of this type. It has been discovered, however, that the catalyst does not function when the metal portion is unsupported or supported on alumina, silica gel, titania, zirconia or an alkaline earth carbonate. Various percentages of metal on the carbon support can be utilized. A preferred range is from about 1% to about 10% by weight, however, higher or lower loadings are also effective.

The process of the instant invention permits continuous production of the isomeric carboxylic acid esters from the cyclic acetals in yields superior to those obtained by known processes such as those using peroxide or photochemical means to induce the reaction. The production rate of carboxylic acid esters by this method is much higher than can be obtained with peroxide or photochemically induced reactions because of the short reaction time which can be used with the novel platinum group metal-carbon catalyzed rearrangement.

The significance of the novel catalyst is further demonstrated by comparison with the results disclosed by Fleury. For example, 5,5-dimethyl-2-ethyl-1,3-dioxolane is reported to be stable to thermal rearrangement at 600° C. by Fluery. According to the process of the instant invention, 5,5-dimethyl-2-ethyl-1,3-dioxolane will rearrange to produce neopentyl isobutyrate in 90 percent yield when contacted with 5% platinum on carbon at a temperature of about 300° C. (Table I, Example 5)

The anticipated product from a thermal decomposition of an acetal would be an unsaturated ether, aldehyde or alcohol. See for example the work reported by Sigmund and Hershodorfer [Montash, 58, 268, (1931)] and Rondestvedt and Mantell, [J. Amer. Chem. Soc., 84, 3307 (1962)].

The rearrangement as demonstrated by the subject invention has considerable utility. For example, the reaction will allow the conversion of an aldehyde to an ester without a carboxylic acid intermediate or without the use of oxidizing gases or typical oxidizing reagents. Similarly, the reaction allows the reduction of a glycol to an alcohol in a very selective manner without the use of the normal reducing agents. The usefulness of this rearrangement is shown by the formation of 2,2,4-trimethylpentyl isobutyrate from the acetal of 2,2,4-trimethylpentane-1,3-diol and isobutyraldehyde.

The process of the instant invention is illustrated in greater detail by the following examples. It is understood that these examples are not intended to limit the invention and obvious modifications will occur to those skilled in the art.

The examples in this section include data for rearrangement of six cyclic acetals and two attempted rearrangements of acyclic acetals as summarized in Table I.

The yield of carboxylic acid esters from the six cyclic acetals ranged from 50 percent to 90 percent. The conversion of acetals as, calculated by the equation (percent conversion = 1 − mole fraction acetal unreacted × 100), ranged from 70 percent to 99 percent and was dependent on the temperature and residence time in the reactor.

The catalyst for the examples shown was 5 percent platinum on 4 × 8 mesh pelletized activated carbon.

The reaction conditions described for Examples 1 and 2 were also used in Examples 3 through 8.

In Example 1, the rearrangement of 2-isopropyl-1,3-dioxolane to ethyl isobutyrate, demonstrates a typical rearrangement of a simple cyclic acetal to the corresponding ester. Examples 2 and 3 demonstrate that primary esters are formed in preference to secondary esters when the glycol portion of the acetal contains a primary and a secondary hydroxyl group. Example 4 demonstrates that hydroxy substitution on the acetal survives the rearrangement. Similarly, Example 5 demonstrates the fact that acetoxy functionality survives the rearrangement conditions and shows an increased yield over the hydroxy compound.

The rearrangement of diethylisobutyral (Example 7) and 2-methoxytetrahydropyran (Example 8) resulted in the formation of unsaturated ethers, illustrating the fact that a cyclic acetal structure is required for rearrangement to carboxylic acid esters to occur.

EXAMPLE 1

Rearrangement of 2-Isopropyl-1,3-dioxolane

The purpose of this example is to demonstrate the rearrangement of a simple cyclic acetal to the corresponding ester. A Pyrex tube 1 inch by 36 inches is packed with 10 grams (20 milliliters) of 5 percent platinum on 4 by 8 mesh carbon supported and covered with Berl saddles. The cyclic acetal, 2-isopropyl-1,3-dioxolane is fed over the catalyst at 60 milliliters (0.52 mole) per hour with 200 milliliters per minute of hydrogen. The contact time is calculated to be 2.1 seconds. The tube is maintained at 300° C. The product consists of 62 weight percent ethyl isobutyrate (73.2 percent yield) and 15.4 percent isobutyric acid. The acetal conversion is 84.6 percent. The weight hourly space velocity (WHSV) is 1,655 grams per hour per liter of catalyst.

EXAMPLE 2

Rearrangement of 2,4-Diisopropyl-5,5-dimethyl-1,3-dioxane 2,4-Diisopropyl-5,5-dimethyl-1,3-dioxane is fed over the catalyst of Example 1 at 60 milliliters per hour (0.3 mole). The temperature is maintained at 320° C. The product consists of 77 weight percent 2,2,4-trimethylpentylisobutyrate, 5 weight percent 2,2,4,4-tetramethylbutylisobutyrate, 3 weight percent 2,3,4-trimethylpentylisobutyrate, 2 weight percent 2,2,4-trimethyl-3-pentenylisobutyrate, 4 weight percent isobutyric acid, and 2 weight percent 2,3,4-trimethylpentane. The conversion of acetal to products is 97 percent. The yield of 2,2,4-trimethylpentylisobutyrate is 80 percent. The contact time is 3.8 seconds and the WHSV is 2,000 grams per hour per liter of catalyst.

Examples 3 through 8 are conducted in the same fashion as Examples 1 and 2 utilizing various reactants as shown in Table I. The reactants, products, yields, conversions and reaction temperatures are shown in Table I.

TABLE I

| Example | Reactant | Product | % Yield | % Convn. | Temp. ° C. |
|---|---|---|---|---|---|
| 1 | 2-Isopropyl-1,3-dioxolane | Ethyl isobutyrate | 73 | 85 | 300 |
| 2 | 5,5-Dimethyl-2,4-diisopropyl-1,3-dioxane | 2,2,4-Trimethylpentyl isobutyrate | 80 | 97 | 320 |
| 3 | 4-Methyl-2-isopropyl-1,3-dioxolane | n-Propylisobutyrate | 74 | 70 | 240 |
| 4 | 2(1,1-Dimethyl-2-hydroxy ethyl)-1,3-dioxolane | Ethyl hydroxypivalate | 50 | 99 | 290 |
| 5 | 2(1,1-Dimethyl-2-acetoxy | Ethyl acetoxypivalate | 80 | 100 | 290 |

TABLE I-continued

| Example | Reactant | Product | % Yield | % Convn. | Temp. °C. |
|---|---|---|---|---|---|
| 6 | ethyl)-1,3-dioxolane 5,5-Dimethyl-2-ethyl-1,3-dioxane | Neopentyl propionate | 90 | 99 | 290 |
| 7 | 2-Methoxytetrahydropyran | 2,3-Dihydropyran and methanol | 61 | 97 | 250-300 |
| 8 | Diethyl isobutyral | Ethyl isobutenylether and ethanol | 62 | 98 | 250-300 |

EXAMPLE 9

The purpose of this example is to demonstrate the rearrangement of 2,4-diisopropyl-5,5-dimethyl-1,3-dioxane using palladium on carbon as the catalyst.

2,4-Diisopropyl-5,5-dimethyl-1,3-dioxane is fed over 10 grams (20 milliliters) of 4.2 percent palladium on 4 × 8 mesh carbon at 60 milliliters (0.3 mole) per hour with 200 milliliters of hydrogen. The temperature is maintained at 300° C. The product contains 11 weight percent 2,2,4-trimethylpentyl isobutyrate. The acetal conversion is 20 percent. The WHSV is 270 grams per hour per liter of catalyst.

The invention has been described in detail with particular reference to preferred embodiments thereof, but it will be understood that variations and modifications can be effected within the spirit and scope of the invention as described hereinabove and in the appended claims.

I claim:

1. A catalyzed method for the rearrangement of a cyclic acetal having the formula

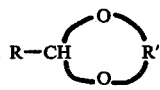

to an isomeric carboxylic acid ester wherein R is an alkyl, alkenyl, phenyl or alkyl substituted phenyl moiety containing 1 to 12 carbon atoms, and R' is alkyl or alkenyl moiety containing 1 to 12 carbon atoms, whereby the cyclic acetal is contacted with a catalytically effective amount of a metal selected from the group Ru, Rh, Pd, Os, Ir or Pt supported on carbon at a temperature of from about 200° C. to about 400° C.

2. A process according to claim 1 wherein the cyclic acetal is contacted with Pt supported on carbon.

3. A process according to claim 1 wherein the reaction is conducted by passing the vapors of the cyclic acetal over the catalyst.

4. A process according to claim 1 wherein the reaction is conducted at a temperature of from about 250° C. to about 350° C.

5. A process according to claim 1 wherein the reaction is conducted with the cyclic acetal in a liquid phase.

6. A process according to claim 5 wherein the reaction is conducted at a temperature of from about 100° C. to about 400° C.

7. A process according to claim 6 wherein the reaction is conducted at a temperature of from about 200° C. to about 350° C.

8. A process according to claim 1 wherein the cyclic acetal is 2,4-diisopropyl-5,5-dimethyl-1,3-dioxane and the resultant carboxylic acid ester is 2,2,4-trimethylpentyl-isobutyrate.

9. A process according to claim 1 wherein the cyclic acetal is 2-(1,1-dimethyl-2-hydroxyethyl)-1,3-dioxolane and the resultant carboxylic acid ester is ethyl hydroxypivalate.

* * * * *